United States Patent
Liu et al.

(10) Patent No.: US 10,807,957 B2
(45) Date of Patent: Oct. 20, 2020

(54) TETRADENTATE CHELATING MONOQUINOLINE DERIVATIVE, MANUFACTURING METHOD THEREOF, AND APPLICATION OF SAME AS METAL ION REGULATOR FOR NEURODEGENERATIVE DISEASE

(71) Applicants: GUANGDONG UNIVERSITY OF TECHNOLOGY, Guangzhou (CN); the Centre National de la Recherche Scientifique, Paris (FR)

(72) Inventors: Yan Liu, Guangzhou (CN); Xingguo Liu, Guangzhou (CN); Weixin Zhang, Guangzhou (CN); Daya Huang, Guangzhou (CN); Meijie Huang, Guangzhou (CN); Dean Wang, Guangzhou (CN); Ju Huang, Guangzhou (CN); Siwei Shu, Guangzhou (CN); Michel Nguyen, Toulouse (FR); Anne Robert, Toulouse (FR); Bernard Meunier, Toulouse (FR)

(*) Notice: Subject to any disclaimer, the term of this patent is extended or adjusted under 35 U.S.C. 154(b) by 0 days.

(21) Appl. No.: 16/199,148

(22) Filed: Nov. 24, 2018

(65) Prior Publication Data

US 2019/0092730 A1   Mar. 28, 2019

Related U.S. Application Data

(63) Continuation of application No. PCT/CN2017/085886, filed on May 25, 2017.

(30) Foreign Application Priority Data

May 27, 2016 (CN) .......................... 2016 1 0369550

(51) Int. Cl.
| | | |
|---|---|---|
| *C07D 215/40* | (2006.01) | |
| *A61K 31/47* | (2006.01) | |
| *A61P 25/28* | (2006.01) | |
| *A61P 25/16* | (2006.01) | |

(52) U.S. Cl.
CPC ............ *C07D 215/40* (2013.01); *A61K 31/47* (2013.01); *A61P 25/16* (2018.01); *A61P 25/28* (2018.01); *Y02P 20/55* (2015.11)

(58) Field of Classification Search
CPC ........ C07D 215/40; A61K 31/47; A61P 25/28
See application file for complete search history.

(56) References Cited

U.S. PATENT DOCUMENTS

| 6,277,841 B1 | 8/2001 | Rajagopalan et al. |
| 7,589,209 B2 | 9/2009 | Canary et al. |
| 2014/0364454 A1 | 12/2014 | Gaboriau et al. |

FOREIGN PATENT DOCUMENTS

| CN | 1128763 A | 8/1996 |
| CN | 105949120 A | 9/2016 |
| WO | 9007376 A | 7/1990 |

OTHER PUBLICATIONS

Zhang, Chem Eur J, vol. 24, 7825-7829, 2018. (Year: 2018).*
Huang, Eur J Inorg Chem, 1384-1388, 2019. (Year: 2019).*
NIH document "What are common treatments for Down syndrome?", https://www.nichd.nih.gov/health/topics/down/conditioninfo/treatments#drugs, Jan. 31, 2017. (Year: 2017).*
Cerpa, Moleculat Aspects of MEdicine, vol. 26, 405-420, 2005. (Year: 2005).*
Zhang, C.R.Chimie, vol. 21, 475-483, 2018. (Year: 2018).*
Internation Search Report of PCT/CN2017/085886, dated Aug. 18, 2017.
P. Faller, C. Hureau, Chem. Eur. J., 012, 18, 15910-15920.
M. A. Telpoukhovskaia, C. Orvig, Chem. Soc. Rev., 2013, 42, 1936-1846.
R. A. Cherny et al. Neuion, 2001, 30, 665-676.
K. J. Barnham and A. I. Bush, Chem. Soc. Rev., 2014, 43, 6727-6749.
Barnham and Bush, Chem. Soc. Rev., 2014, 43, 6727-6749.
Perez and Franz, Dalton Trans., 2010, 39, 2177-2187.
Rowinska-Zyrek et al., Coord. Chem. Rev., 2015, 284, 298-312.
Robert et al., Acc. Chem, Res. 2015, 48, 1332-1339.
Bandmann et al., Lancet Neurol., 2015, 14, 103-113.

* cited by examiner

*Primary Examiner* — D Margaret M Seaman
(74) *Attorney, Agent, or Firm* — Erson IP (Nelson IP)

(57) ABSTRACT

A tetradentate chelating monoquinoline derivative with a structure as shown in formula (I) is able to specifically chelate redox active metal ions like copper ions that are dis-regulated in neurodegenerative diseases (Alzheimer's disease, Huntington's disease, Parkinson's disease, and amyotrophic lateral sclerosis), or copper accumulation disease like Wilson's disease. The binding constants of these derivatives for zinc are 6-10 orders of magnitude below that ones for copper, and these derivatives have a good capability of reducing an oxidative stress. The method for preparing the derivative is simple and the derivatives have good application prospects in manufacturing drugs for neurodegenerative diseases and diseases related to disorder of copper metabolism.

3 Claims, 2 Drawing Sheets

TETRADENTATE CHELATING MONOQUINOLINE DERIVATIVE, MANUFACTURING METHOD THEREOF, AND APPLICATION OF SAME AS METAL ION REGULATOR FOR NEURODEGENERATIVE DISEASE

CROSS-REFERENCE TO RELATED APPLICATIONS

This application is a continuation of International Patent Application No. PCT/CN2017/085886 with a filing date of May 25, 2017, designating the United States, now pending, and further claims priority to Chinese Patent Application No. 201610369550.X with a filing date of May 27, 2016. The content of the aforementioned applications, including any intervening amendments thereto, are incorporated herein by reference.

TECHNICAL FIELD

The present disclosure relates to the field of medication and organic synthesis techniques, novel monoquinoline derivatives, and more particularly to a tetradentate chelating monoquinoline derivative, a manufacturing method thereof, and an application of the same as a metal ion regulator for neurodegenerative disease.

BACKGROUND OF THE PRESENT INVENTION

Various scientific journals reported that many progressive and neurodegenerative multi-genic diseases are associated with a dysregulation or an excessive accumulation of metal ions. It is also the case for some monogenic diseases. As an example, in Alzheimer's disease (AD), the accumulation of copper ions in amyloid peptides in the brain of patients due to rupture of the homeostasis of copper in AD brains, is at the origin of an oxidative stress that might induce neuron death.

Different scientific articles have also mentioned that redox active metal ions (copper or iron) are involved in the misfolding and/or aggregation of proteins leading to serious pathologies, for example: Alzheimer's disease, Parkinson's disease, Huntington's disease, amyotrophic lateral sclerosis, spongiform encephalopathies, etc. In the different pathologies, the rupture of the homeostasis of the redox active metal ions that are easily reduced by endogenous reductants (or adventitious electron source) might be at the origin of the metal-mediated reduction of molecular oxygen, leading to the production of reactive oxygen species (ROS) such as hydrogen peroxide and finally hydroxyl radicals (P. Faller, C. Hureau, *Chem. Eur. J.*, 2012, 18, 15910-15920; M. A. Telpoukhovskaia, C. Orvig, *Chem. Soc. Rev.*, 2013, 42, 1836-1846).

Among different chelators, clioquinol and PBT2 are two monoquinoline derivatives that have been used as potential therapeutic agents in Alzheimer's disease (R. A. Cherny et al. *Neuron*, 2001, 30, 665-676; K. J. Barnham and A. I. Bush, *Chem. Soc. Rev.*, 2014, 43, 6727-6749; see also WO 2004/007461). However, these monoquinoline compounds are only bidentate ligands that are unable to efficiently remove copper ion linked to amyloids. Such bidentate ligands are forming ternary complex "amyloid-copper-clioquinol" as recently evidenced (M. Nguyen et al., *ChemistryOpen*, 2014, 20, 6771-6785). The same article has evidenced the necessity to have a tetradendate ligand to extract copper from amyloid.

For recent review articles, see Barnham and Bush, *Chem. Soc. Rev.*, 2014, 43, 6727-6749, Perez and Franz, *Dalton Trans.*, 2010, 39, 2177-2187, Rowinska-Zyrek et al., *Coord. Chem. Rev.*, 2015, 284, 298-312, Robert et al., *Acc. Chem. Res.* 2015, 48, 1332-1339, Bandmann et al., *Lancet Neurol.*, 2015, 14, 103-113.

However, few reports have been proposed at present that the monoquinoline compounds are able to specifically extract copper ion linked to amyloids.

SUMMARY OF PRESENT INVENTION

In one aspect, an objective of the present disclosure is to provide mono-8-aminoquinoline tetradendate derivatives that have a high selectivity for the chelation of copper ions, a required property for compounds that should regulate the copper homeostasis in neurodegenerative diseases, like Alzheimer's disease, Huntington's disease, Parkinson's disease, Down syndrome or amyotrophic lateral sclerosis as an example, and also in monogenic disease related to the absence of a copper carrier protein like the Wilson's disease. As disclosed in the present disclosure, chelators based on monoquinoline derivatives should have a suitable hydrophobicity in order to be active by oral administration and to be able to cross the blood-brain barrier. These ligands are abbreviated as TDMQ for tetradendate monoquinolines.

More precisely, the compounds according to the present disclosure are metal ligands able to specifically chelate redox active metal ions like copper ions that have been found in excess in amyloid peptides in the brain of AD patients. As used in the description herein and throughout the claims that follow, AD stands for Alzheimer's disease. The compounds described in this disclosure are also applicable to other neurodegenerative diseases associated with a dysregulation of other metal ions like Parkinson's disease (PD) and amyotrophic lateral sclerosis (ALS). In addition, a monogenic disease like Wilson's disease (WD) leading to an over-loading of copper ions in blood circulation and different organs is also a domain of application of these chelating ligands.

In another aspect, an objective of the present disclosure is to provide a manufacturing method and an application of above-mentioned derivatives.

In order to have the lower as possible molecular weight of such tetradentate ligands (for possible better biodisponibility parameters), we decided to design a series of new drugs based on a mono-aminoquinoline skeleton.

Here we report the synthesis, the chelating behavior and the capacity of inhibiting the oxidative stress induced by the copper complex of amyloid peptides, by using, as an example, the reduction of the production of hydrogen peroxide by copper-amyloids in the presence of a reducing agent.

Aiming at above objectives, technical solutions are provided as follows:

A tetradentate chelating monoquinoline derivative is provided, and a structure of the derivative is as shown in formula (I):

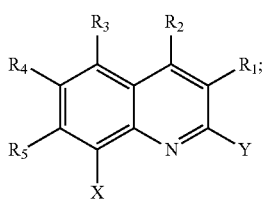

formula (I)

X represents a NRR' group;
Y represents a group with the following formula:
—$(CH_2)_n$—$NR_6$—$(CH_2)_m$—$NR_7R_8$; n represents 1 or 2 or 3 or 4 or 5, m represents 1 or 2 or 3 or 4 or 5;
R and R' are the same or different and independently represent a hydrogen atom, or an alkyl or cycloalkyl with one or more groups replaced with an alkoxy radical, an amine radical, a —$CF_3$, a halogen atom, a —CN, an ester radical and/or an acylamino radical;
$R_1$, $R_2$, $R_3$, $R_4$, $R_5$, $R_6$, $R_7$ and $R_8$ are the same or different and independently represent a group or an atom selected from H or an alkoxy radical or an amine radical or a halogen atom or a —CN or a —$CF_3$ or an ester radical or an acylamino radical, or represent alkyl with one or more groups replaced with an alkoxy radical or an amine radical, a halogen atom, a —CN, a —$CF_3$, an ester radical and/or an acylamino radical.

Advantageously, X represents the NRR' group; Y represents
—$(CH_2)_n$—$NR_6$—$(CH_2)_m$—$NR_7R_8$; R and R' are the same or different and independently represent a hydrogen atom, or an alkyl or cycloalkyl with one or more groups replaced with an amine radical, a halogen atom, a —CN and/or a —$CF_3$; $R_1$, $R_2$, $R_3$, $R_4$, $R_5$, $R_6$, $R_7$ and $R_8$ are the same or different and independently represent a group or an atom selected from H or an alkoxy radical or an amine radical or a halogen atom or a —CN or a —$CF_3$, or represent alkyl with one or more groups replaced with an alkoxy radical or an amine radical or a halogen atom or —CN and/or —$CF_3$.

Advantageously, X represents the NRR' group; Y represents
—$(CH_2)_n$—$NR_6$—$(CH_2)_m$—$NR_7R_8$; R and R' are the same or different and independently represent a hydrogen atom, or an alkyl or cycloalkyl with one or more groups replaced with an amine radical, a halogen atom, a —CN and/or a —$CF_3$; $R_1$, $R_2$, $R_3$, $R_4$, $R_5$, $R_6$, $R_7$ and $R_8$ are the same or different and independently represent H or an alkyl with one or more groups replaced with an alkoxy radical or an amine radical or a halogen atom or a —CN and/or a $CF_3$.

Advantageously, X represents an —$NH_2$.

Interpretation of Terms

The present disclosure relates to the compounds including the pharmaceutically acceptable stereoisomers or mixtures, tautomeric forms, hydrates, solvates, salts (salts include hydrochloride, hydrobromide, sulfate, bisulfate, phosphate, nitrate, acetate, benzoate, tosylate, citrate, maleate, tartrate, and the like), free base forms and esters thereof.

According to the present disclosure, the alkyl radicals are linear or branched saturated hydrocarbon radicals, containing from 1 to 20 carbon atoms, preferably from 1 to 6 carbon atoms.

The methyl, ethyl, propyl, butyl, pentyl, hexyl, octyl, nonyl, decyl, dodecyl, hexadecyl and octadecyl radicals can be mentioned in particular as linear radicals.

The isopropyl, tert-butyl, 2-ethylhexyl, 2-methylbutyl, 2-methylpentyl, 1-methylpentyl and 3-methylheptyl radicals can be mentioned in particular as branched radicals.

Alkoxy radicals are radicals of formula —O-alkyl, and the alkyl is as defined hereinbefore.

Fluorine, chlorine and bromine atoms are mentioned in particular as halogen atoms.

The alkenyl radicals are linear or branched and comprise one or more double carbon-carbon bonds.

The alkynyl radicals are linear or branched and comprise one or more triple carbon-carbon bonds.

The cycloalkyl radical is a saturated or partially unsaturated monocyclic, bicyclic or tricyclic, hydrocarbon radical containing from 3 to 11 carbon atoms, such as, in particular, cyclopropyl, cyclopentyl, cyclohexyl or adamantyl, as well as the corresponding rings containing one or more unsaturated bonds.

The term aryl denotes a monocyclic or bicyclic hydrocarbon aromatic system containing from 6 to 10 carbon atoms, such as, in particular, phenyl or naphthyl radical, substituted or not by halogen atoms.

Heteroaryl radicals denotes aromatic systems comprising one or more heteroatoms selected from nitrogen, oxygen or sulfur, mono- or bicyclic, which contain from 4 to 11 carbon atoms, such as, in particular and as examples, pyrazinyl, thienyl, oxazolyl, furazanyl, pyrrolyl, 1,2,4-thiadiazolyl, azaindolyl, benzimidazolyl, furanyl, imidazolyl, indolyl, tetrazolyl, isoquinolinyl, pyrazolyl, quinolinyl, isoquinolinyl, thiazolyl.

The term "pharmaceutical acceptable salts" refers to relatively non-toxic, inorganic or organic salts of compounds of the present invention. These salts can be prepared in situ during the final isolation or purification of the compounds. Examples of acid addition salts include bromide, chloride, sulfate, phosphate, nitrate, acetate, oxalate, borate, tosylate, citrate, maleate, fumarate, mesylate, methanesulfonate, p-toluenesulfonate, as a non-limited list.

Advantageously, the tetradentate chelating monoquinoline derivative [general formula (I)] is prepared according to the following synthesis scheme and a method comprising the following steps:

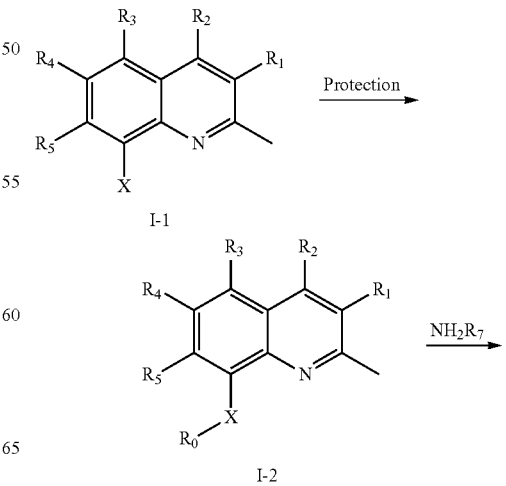

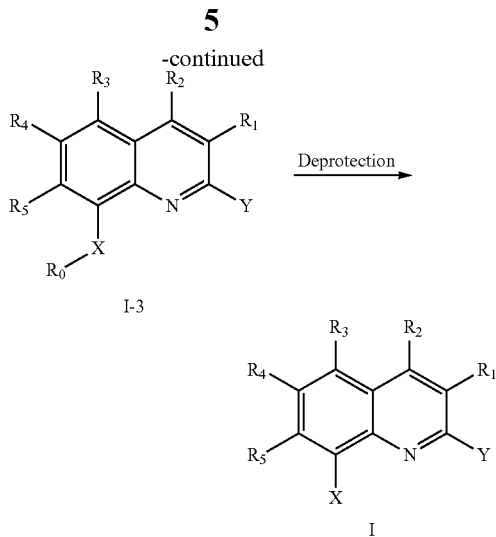

S1. protecting X group of a compound I-1 to form a compound I-2, wherein; $R_0$ represents a protecting group for the X group and comprises but not limited to a tert-butyloxycarbonyl group and a acetyl group;

S2. functionalizing the compound I-2, followed by reacting with amine-containing derivatives to generate compound I-3; and S3. deprotecting the compound I-3 to yield the final monoquinoline derivative.

The present invention have thus developed the tetradentate chelating monoquinoline derivatives with better specific metal ion chelating behavior and capacity of inhibiting an oxidative stress. Especially, the tetradentate chelating monoquinoline derivatives are able to strongly chelate copper ions, and with a suitable hydrophobicity in order to be active by oral administration and to be able to cross the blood-brain barrier. Through complexation studies concerning the derivatives and copper or zinc ions, and the calculation of affinity constants, it finds that the binding constant for copper log $K_{cu}^{2+}$ is always greater than 9.5 and the binding constant for zinc log $K_{zn}^{2+}$ is never greater than 4.7, which indicates that the tetradentate chelating monoquinoline derivatives developed in the present invention have strongly specific metal ion chelating behavior, and meanwhile are better ligands for manufacturing drugs for neurodegenerative diseases. Through the experiments on the production of hydrogen peroxide by amyloid-β in the presence of copper ions and a reducing agent, it finds that the tetradentate chelating monoquinoline derivatives in the present invention are able to extract copper ion from copper-amyloid complex and exhibit a strong capability of reducing an oxidative stress.

Thus, the use of the tetradentate chelating monoquinoline derivatives for preparing the complexation of metal ions is claimed. The monoquinoline derivatives are able to specifically chelate copper ions for preparing the complexation of metal ions.

An application of the tetradentate chelating monoquinoline derivatives in manufacturing metal ion regulator for neurodegenerative diseases is claimed. The application of the tetradentate chelating monoquinoline derivatives in manufacturing drugs for curing neurodegenerative diseases and diseases related to disorder of copper metabolism.

Advantageously, the tetradentate chelating monoquinoline derivative further comprises pharmaceutically acceptable stereoisomers or mixtures, tautomeric forms, hydrates, solvates, salts, free base forms and esters thereof; and the salts include hydrochloride, hydrobromide, sulfate, bisulfate, phosphate, nitrate, acetate, benzoate, tosylate, citrate, maleate or tartrate.

Advantageously, the neurodegenerative diseases include Alzheimer's disease, Huntington's disease, Parkinson's disease, Down syndrome, or amyotrophic lateral sclerosis, and diseases related to disorder of copper metabolism comprising Wilson's disease.

Compared with the prior art, the present invention has the following advantages:

The tetradentate chelating monoquinoline derivatives provided in the present disclosure are able to selectively chelate copper ions with the binding constant for copper least 6-10 orders of magnitude above that for zinc, and have better capability of inhibiting an oxidative stress. The method for preparing the tetradentate chelating monoquinoline derivatives is simple and the tetradentate chelating monoquinoline derivatives have good application prospects in manufacturing drugs for neurodegenerative diseases.

DETAILED DESCRIPTION OF PREFERRED EMBODIMENTS

Figure 1:
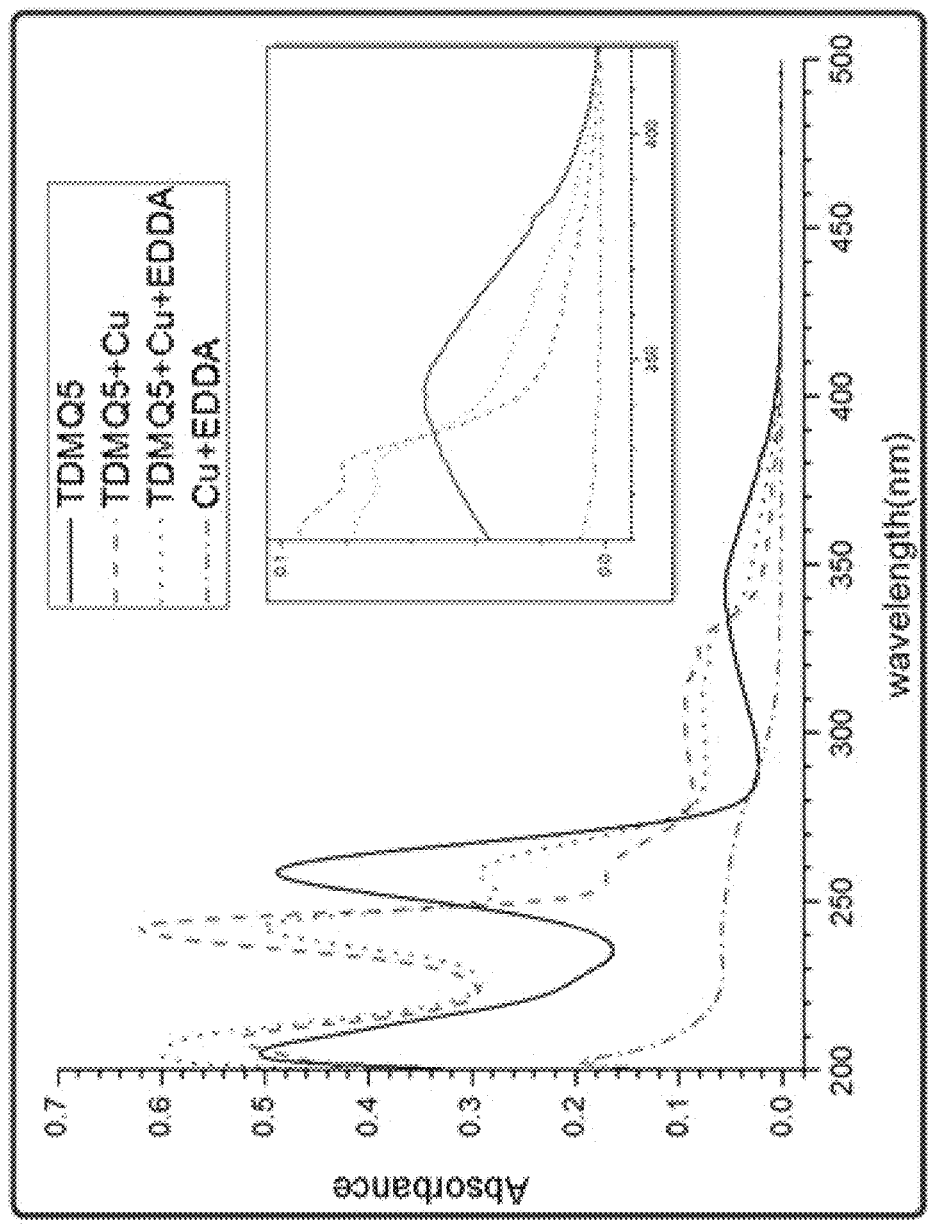
FIG. 1 is an UV-visible spectrum of copper complexes of compound TDMQ-5, associated with other competing ligands.

The present disclosure will be further described in detail with reference to the accompanying drawings and preferred embodiments below. It should be understood that embodiments described here are only for explaining the present disclosure and the disclosure, however, should not be constructed as limited to the embodiment as set forth herein. Reagents, methods and devices described in the present disclosure are all conventional ones in the art unless the context clearly dictates otherwise.

Reagents and materials used in the following examples are all purchased from the market.

Example 1: Synthesis of TDMQ-5

Synthetic route is shown as follows.

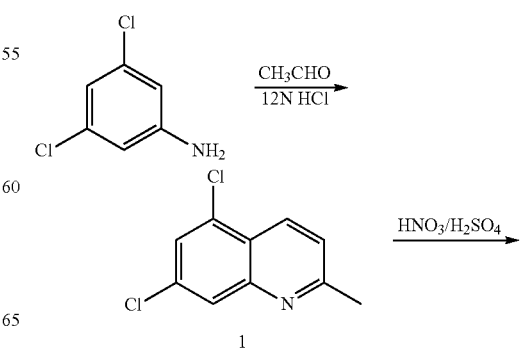

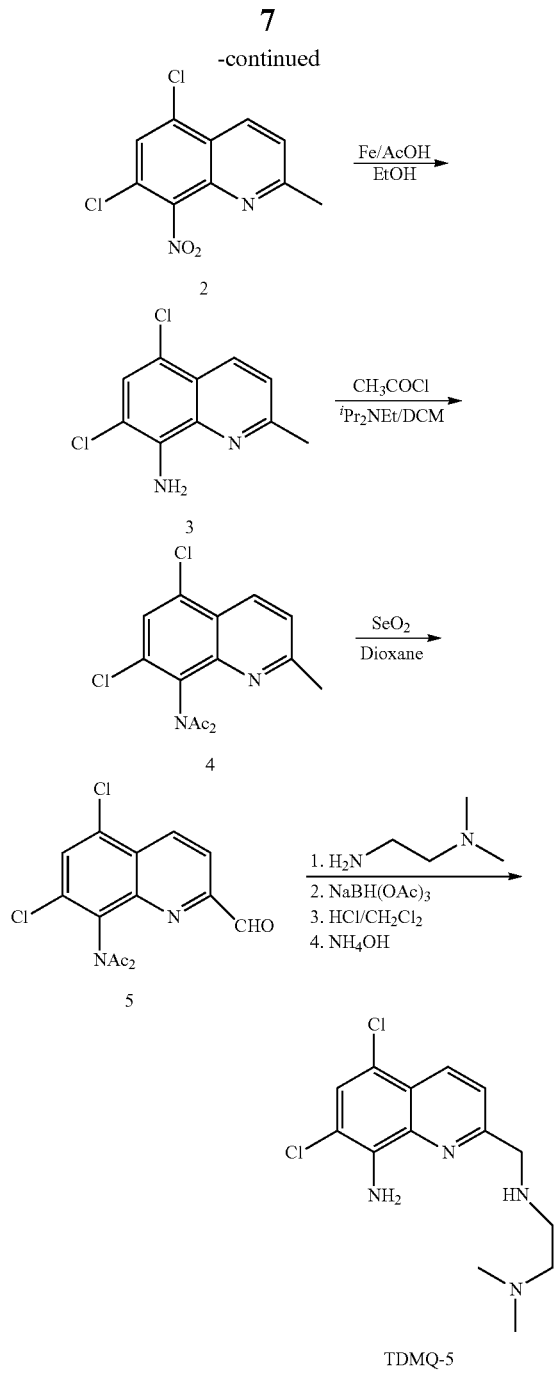

The specific steps are described below.

5,7-dichloro-2-methylquinoline (1)

To a solution of 3,5-dichloroaniline (3.24 g, 20 mmol) in concentrated HCl (12 mL) at 0° C. was added dropwise with stirring acetaldehyde. The reaction medium was kept at 0° C. for 15 min, and the temperature was gradually raised to 75° C. The mixture was stirred at 75° C. for 4 h. The reaction mixture was poured into ice-cold water and neutralized with aqueous ammonium hydroxide. After extraction with $CH_2Cl_2$, the organic phase was dried over $Na_2SO_4$, filtered, and concentrated under reduced pressure. The crude mixture was purified by silica gel flash column chromatography (ethyl acetate/petroleum ether, 1:20, v/v). After evaporation of the eluent, compound 1 was obtained as a light yellow solid (2.93 g, 69%). $^1$H NMR (400 MHz, $CDCl_3$): δ 8.40 (d, J=8.0 Hz, 1H), 7.96 (d, J=2.0 Hz, 1H), 7.55 (d, J=2.0 Hz, 1H), 7.37 (d, J=8.0 Hz, 1H), 2.76 (s, 3H).

5,7-dichloro-2-methyl-8-nitroquinoline (2)

To a stirred solution of compound 1 (2.12 g, 10 mmol) in neat sulfuric acid (10 mL) was added fuming nitric acid (2.0 mL) dropwise over a 1 h period at ambient temperature. The resulting mixture was stirred for an additional hour, and was then poured onto ice. The mixture was allowed to warm to ambient temperature, neutralized with aqueous ammonium hydroxide. After extraction with $CH_2Cl_2$, the organic phase was dried over $Na_2SO_4$, filtered, and concentrated under reduced pressure. The crude mixture was purified by silica gel flash column chromatography (ethyl acetate/petroleum ether, 1:10, v/v). Evaporation of the solvent afforded compound 2 as a yellow solid (2.34 g, 91%). $^1$H NMR (400 MHz, $CDCl_3$): δ 8.43 (d, J=8.0 Hz, 1H), 7.64 (s, 1H), 7.50 (d, J=8.0 Hz, 1H), 2.76 (s, 3H).

5,7-dichloro-2-methylquinolin-8-amine (3)

Iron (1.34 g, 24 mmol) and acetic acid (18 mL) were added to a solution of compound 2 (2.06 g, 8 mmol) in ethanol (50 mL). The mixture was stirred at reflux for 4 h. The mixture was added dropwise over a saturated aqueous solution of $NaHCO_3$ (400 mL) and extracted with $CH_2Cl_2$ (3×200 mL). The combined organic layers were dried ($Na_2SO_4$), filtered and concentrated under reduced pressure. The crude product was purified by silica gel flash chromatography (ethyl acetate/petroleum ether, 1:10, v/v). Evaporation of the solvent afforded compound 3 as a light yellow solid (1.62 g, 89%). $^1$H NMR (400 MHz, $CDCl_3$): δ 8.31 (d, J=8.0 Hz, 1H), 7.42 (s, 1H), 7.35 (d, J=8.0 Hz, 1H), 5.36 (brs, 2H), 2.76 (s, 3H).

N-acetyl-N-(5,7-dichloro-2-methylquinolin-8-yl) acetamide (4)

To a solution of compound 3 (1.29 g, 5 mmol) in $CH_2Cl_2$ (10 mL) was added acetyl chloride (1.1 mL) and N,N-diisopropylethylamine (5 mL) at 0° C. The reaction medium was kept at 0° C. for 15 min, and was gradually raised to reflux. The mixture was stirred at reflux for 4 h and then the solvent was removed under reduced pressure. The crude mixture was purified by silica gel flash column chromatography (ethyl acetate/petroleum ether, 1:20, v/v). After evaporation of the eluent, compound 4 was obtained as a light yellow solid (1.09 g, 70%). $^1$H NMR (400 MHz, $CDCl_3$): δ 8.41 (d, J=8.0 Hz, 1H), 7.70 (s, 1H), 7.42 (d, J=8.0 Hz, 1H), 2.71 (s, 3H), 2.29 (s, 6H).

N-acetyl-N-(5,7-dichloro-2-formylquinolin-8-yl) acetamide (5)

To a solution of compound 4 (0.93 g, 3 mmol) in 1,4-dioxane (7 mL) was added selenium dioxide (0.5 g, 4.5 mmol). The reaction mixture was heated at 85° C. and stirred for 12 h. The reaction mixture was filtered through a celite column and selenium metal was washed with dichloromethane. The combined filtrates were evaporated to dryness under reduced pressure. The residue was purified by silica gel flash column chromatography (ethyl acetate/petroleum ether, 1:20, v/v). After evaporation of the eluent, compound 5 was obtained as a light yellow solid (0.69 g, 71%). $^1$H NMR (400 MHz, CDCl$_3$): δ 10.13 (s, 1H), 8.76 (d, J=8.0 Hz, 1H), 8.18 (d, J=8.0 Hz, 1H), 7.92 (s, 1H), 2.32 (s, 6H).

$N^1$-((8-amino-5,7-dichloroquinolin-2-yl)methyl)-$N^2$, $N^2$-dimethylethane-1,2-diamine (TDMQ-5)

To a solution of compound 5 (622 mg, 2 mmol) in 1,2-dichloroethane (30 mL) was added N,N-dimethyl-1,2-ethanediamine (352 mg, 4 mmol) under argon. The reaction mixture was stirred at room temperature for 1 h, and sodium triacetoxyborohydride (848 mg, 4 mmol) was added. The resulting mixture was stirred for an additional 12 h, diluted with CH$_2$Cl$_2$ (100 mL), followed by the addition of saturated aqueous sodium bicarbonate solution (40 mL). The organic phase was separated. The aqueous phase was added to 2 mL of ammonium hydroxide, and extracted with CH$_2$Cl$_2$ (3×30 mL). The organic phases were combined, dried over Na$_2$SO$_4$, filtered, and concentrated under reduced pressure. To the crude product in CH$_2$Cl$_2$ (5 mL) was added 6M HCl (2 mL), which was stirred at room temperature for 4 h. Water (50 mL) was added, followed by addition of aqueous 25% ammonium hydroxide. The mixture was extracted with CH$_2$Cl$_2$ (3×30 mL). The combined organic layers were dried (Na$_2$SO$_4$), filtered and concentrated under reduced pressure. The crude product was purified by silica gel flash chromatography (ethyl acetate/isopropanol/ammonium hydroxide (25%), 8:2:0.5, v/v/v). Evaporation of the solvent afforded TDMQ-5 as a light yellow solid (488 mg, 78%).

The structural formula of the compound TDMQ-5 is as follows:

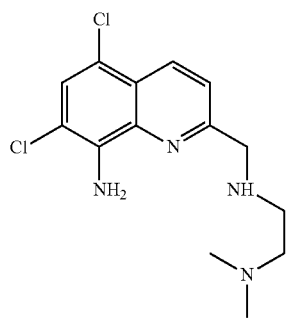 [SMILES: CN(C)CCNCc1ccc2c(Cl)cc(Cl)c(N)c2n1]

$^1$H NMR (400 MHz, CDCl$_3$): δ 8.35 (d, J=8.8 Hz, 1H), 7.49 (d, J=8.8 Hz, 1H), 7.43 (s, 1H), 5.38 (brs, 2H), 4.10 (s, 2H), 2.75 (t, J=6.0 Hz, 2H), 2.55 (brs, 1 H), 2.48 (t, J=6.0 Hz, 2H), 2.22 (s, 6H).

ESI$^+$-MS: m/z (relative intensity) 313.1 (MH$^+$, 100), 314.1 (18), 315.1 (65), 316.1 (11), 317.1 (11), 318.1 (2). Minor peaks due to fragmentation in the mass spectrometer were detected at m/z 268.0 {M'=[M–(CH$_3$)$_2$N]$^+$, 9}, 224.9 {M"=[M–(CH$_3$)$_2$N—(CH$_2$)$_2$—NH]$^+$, 15}, 190.0 (M"–Cl, 5), 155.0 (M"–2 Cl, 3). Isotopic patterns are consistent. HRMS (ESI$^+$) for C$_{14}$H$_{19}$N$_4$Cl$_2$: Calcd, 313.0987; Found, 313.0987.

Calculated log P=2.42 (ChemDraw Pro, v. 14.0).

Example 2: Synthesis of TDMQ-9

Synthetic route is shown as follows.

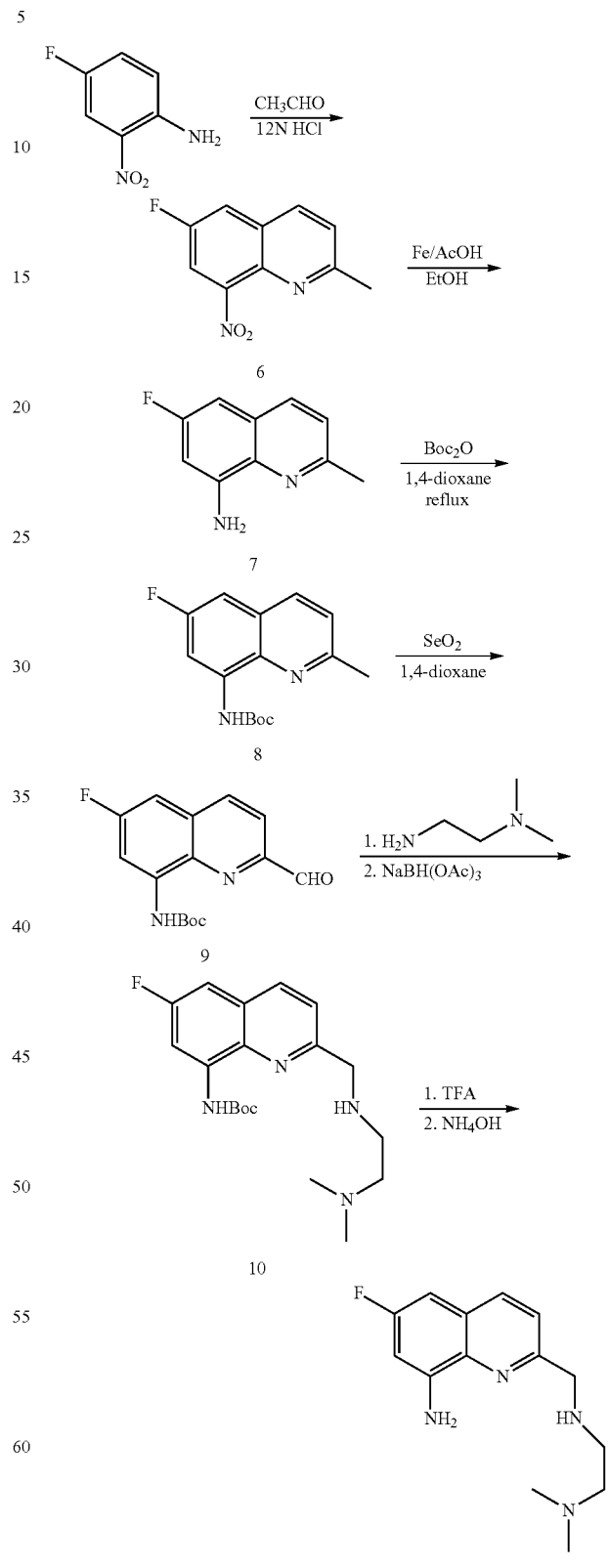

The specific steps are described below.

6-fluoro-2-methyl-8-nitroquinoline (6)

The procedure was similar to that described for the preparation of compound 1. Compound 6 was obtained as a light yellow solid (73%). $^1$H NMR (400 MHz, CDCl$_3$) δ 8.00 (d, J=8.4 Hz, 1H), 7.70 (dd, J=8.0, 2.8 Hz, 1H), 7.55 (dd, J=8.0, 2.8 Hz, 1H), 7.40 (d, J=8.4 Hz, 1H), 2.69 (s, 3H).

6-fluoro-2-methylquinolin-8-amine (7)

The procedure was similar to that described for the preparation of compound 3. Compound 7 was obtained as a light yellow solid (92%). $^1$H NMR (400 MHz, CDCl$_3$) δ 7.87 (d, J=8.4 Hz, 1H), 7.25 (d, J=8.4 Hz, 1H), 6.95 (dd, J=10.8, 2.8 Hz, 1H), 6.63 (dd, J=10.8, 2.8 Hz, 1H), 5.13 (brs, 2H), 2.69 (s, 3H).

tert-butyl (6-fluoro-2-methylquinolin-8-yl)carbamate (8)

To a solution of compound 7 (1.76 g, 10 mmol) in 1,4-dioxane (20 mL) was added di-tert butyl dicarbonate (3.27 g, 15 mmol). The reaction mixture was stirred at reflux for 12 h. After removal of the solvent under reduced pressure, the residue was purified by silica gel flash column chromatography (ethyl acetate/petroleum ether, 1:20, v/v). After evaporation of the eluent, compound 8 was obtained as a white solid (2.58 g, 89%).
$^1$H NMR (400 MHz, CDCl$_3$) δ 9.08 (s, 1H), 8.21 (d, J=10.4 Hz, 1H), 7.94 (d, J=8.4 Hz, 1H), 7.31 (d, J=8.4 Hz, 1H), 6.97 (dd, J=8.8, 2.8 Hz, 1H), 2.72 (s, 3H), 1.59 (s, 9H).

tert-butyl (6-fluoro-2-formylquinolin-8-yl)carbamate (9)

The procedure was similar to that described for the preparation of compound 5. Compound 9 was obtained as a light yellow solid (50%). $^1$H NMR (400 MHz, CDCl$_3$): δ 10.23 (s, H), 9.04 (s, 1H), 8.36 (d, J=10.8 Hz, 1H), 8.23 (d, J=8.4 Hz, 1H), 8.07 (d, J=8.4 Hz, 1H), 7.11 (dd, J=8.4, 2.4 Hz, 1H), 1.62 (s, 9H).

tert-butyl(2-(((2-(dimethylamino)ethyl)amino)methyl)-6-fluoroquinolin-8-yl)carbamate (10)

To a solution of compound 9 (580 mg, 2 mmol) in 1,2-dichloroethane (30 mL) was added N,N-dimethyl-1,2-ethanediamine (352 mg, 4 mmol) under argon. The reaction mixture was stirred at room temperature for 1 h, and sodium triacetoxyborohydride (848 mg, 4 mmol) was added. The resulting mixture was stirred for an additional 12 h and diluted with 100 mL CH$_2$Cl$_2$, followed by the addition of saturated aqueous sodium bicarbonate solution (40 mL). The organic phase was separated. The aqueous phase was added to 2 mL of ammonium hydroxide, and extracted with CH$_2$Cl$_2$ (3×30 mL). The organic phases were combined, dried over Na$_2$SO$_4$, filtered, and concentrated under reduced pressure. After removal of the solvent under reduced pressure, the residue was purified by silica gel flash column chromatography (ethyl acetate/isopropanol/ammonium hydroxide (25%), 8:2:0.5, v/v/v). After evaporation of the eluent, compound 10 was obtained as a light yellow solid (660 mg, 91%). $^1$H NMR (400 MHz, CDCl$_3$): δ 9.07 (s, 1H), 8.25 (d, J=10.0 Hz, 1H), 8.02 (d, J=8.8 Hz, 1H), 7.49 (d, J=8.8 Hz, 1H), 7.0 (dd, J=8.8, 2.8 Hz, 1H), 4.11 (s, 2H), 2.76 (t, J=6.0 Hz, 2H2), 2.49 (t, J=6.0 Hz, 2H), 2.24 (s, 6H), 1.60 (s, 9H).

N$^1$-((8-amino-6-fluoroquinolin-2-yl)methyl)-N$^2$,N$^2$-dimethylethane-1,2-di amine (TDMQ-9)

To compound 10 (725 mg, 2 mmol) in CH$_2$Cl$_2$ (10 mL) was added trifluoroacetic acid (5 mL), which was stirred at room temperature for 4 h. After the removal of extra trifluoroacetic acid, the crude residue was diluted with CH$_2$Cl$_2$, followed by addition of 50 mL water and aqueous 25% ammonium hydroxide (2 mL). The mixture was extracted with CH$_2$Cl$_2$ (3×30 mL). The combined organic layers were dried (Na$_2$SO$_4$), filtered and concentrated under reduced pressure. The crude product was purified by silica gel flash chromatography (ethyl acetate/isopropanol/ammonium hydroxide (25%), 8:2:0.5, v/v/v). After evaporation of the eluent, TDMQ-9 was obtained as a light yellow solid (451 mg, 86%). $^1$H NMR (400 MHz, CDCl$_3$) δ 7.93 (d, J=8.4 Hz, 1H), 7.39 (d, J=8.4 Hz, 1H), 6.71 (dd, J=10.4, 2.8 Hz, 1H), 6.64 (dd, J=10.4, 2.8 Hz, 1H), 5.20 (brs, 2H), 4.07 (s, 2H), 2.85 (brs, 1H), 2.78 (t, J=6.0 Hz, 2H), 2.49 (t, J=6.0 Hz, 2H), 2.23 (s, 6H).

Example 3: Synthesis of TDMQ-10

Synthetic route is shown as follows.

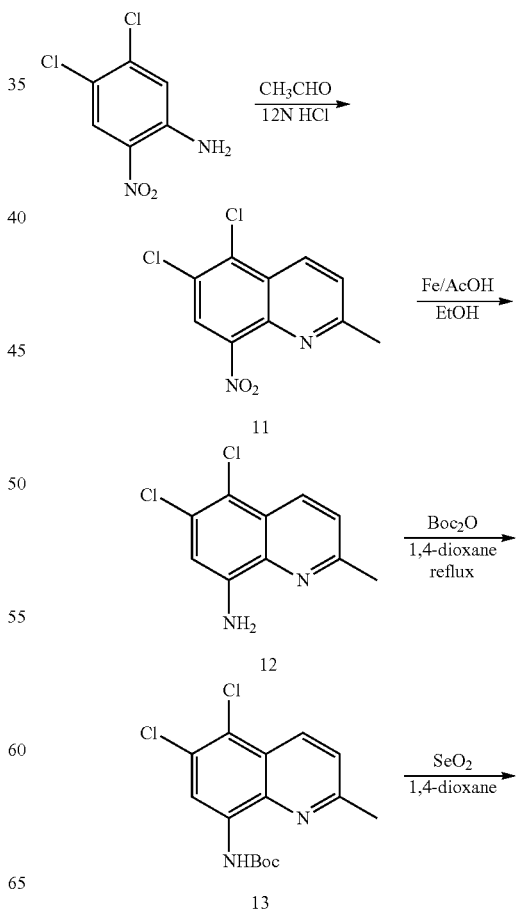

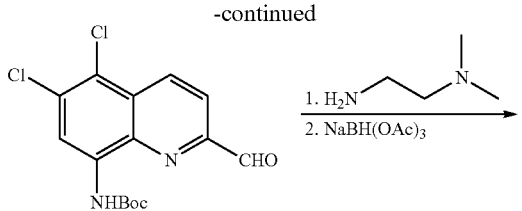

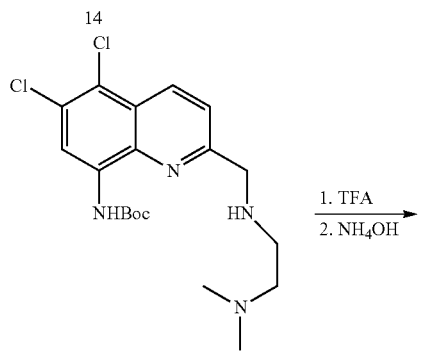

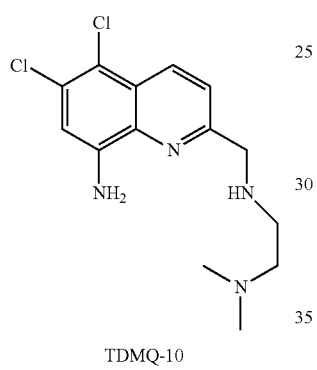

TDMQ-10

The specific steps are described below.

5,6-dichloro-2-methyl-8-nitroquinoline (11)

The procedure was similar to that described for the preparation of compound 1. Compound 11 was obtained as a light yellow solid (54%). $^1$H NMR (400 MHz, CDCl$_3$) δ 8.51 (d, J=8.8 Hz, 1H), 8.03 (s, 1H), 8.16 (d, J=8.8 Hz, 1H), 2.79 (s, 3H).

5,6-dichloro-2-methylquinolin-8-amine (12)

The procedure was similar to that described for the preparation of compound 3. Compound 12 was obtained as a light yellow solid (86%). $^1$H NMR (400 MHz, CDCl$_3$) δ 10.25 (s, H), 8.91 (s, 1H), 8.34 (d, J=8.8 Hz, 1H), 7.37 (d, J=8.8 Hz, 1H), 6.93 (s, 1H), 2.71 (s, 3H).

tert-butyl(5,6-dichloro-2-methylquinolin-8-yl)carbamate (13)

The procedure was similar to that described for the preparation of compound 8. Compound 13 was obtained as a white solid (84%). $^1$H NMR (400 MHz, CDCl$_3$) δ 8.98 (s, 1H), 8.50 (s, 1H), 8.40 (d, J=8.4 Hz, 1H), 7.42 (d, J=8.4 Hz, 1H), 2.75 (s, 3H), 1.59 (s, 9H).

tert-butyl(5,6-dichloro-2-formylquinolin-8-yl)carbamate (14)

The procedure was similar to that described for the preparation of compound 5. Compound 14 was obtained as a light yellow solid (56%). $^1$H NMR (400 MHz, CDCl$_3$) δ 10.25 (s, 1H), 8.91 (s, 1H), 8.69 (d, J=8.4 Hz, 1H), 8.65 (s, 1H), 8.16 (d, J=8.4 Hz, 1H), 1.62 (s, 9H).

tert-butyl(5,6-dichloro-2-(((2-(dimethylamino)ethyl)amino)methyl)quinolin-8-yl)carbamate (15)

The procedure was similar to that described for the preparation of compound 10. Compound 15 was obtained as a light yellow solid (92%). $^1$H NMR (400 MHz, CDCl$_3$): δ 8.97 (s, 1H), 8.54 (s, 1H), 8.48 (d, J=8.8 Hz, 1H), 7.60 (d, J=8.8 Hz, 1H), 4.14 (s, 2H), 2.75 (d, J=6.0 Hz, 2H), 2.48 (d, J=6.0 Hz, 2H), 2.24 (s, 6H), 1.59 (s, 9H).

tert-butyl(5, dichloro-2-(((2-(dimethylamino)ethyl)amino)methyl)quinolin-8-yl) carbamate (TDQM-10)

The procedure was similar to that described for the preparation of TDMQ-9. TDMQ-10 was obtained as a light yellow solid (92%).

The structural formula of the compound TDMQ-10 is as follows:

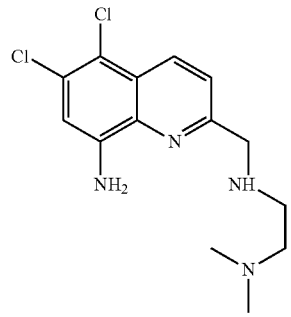 [SMILES: CN(C)CCNCc1ccc2c(Cl)c(Cl)cc(N)c2n1]

$^1$H NMR (400 MHz, CDCl$_3$) δ 8.41 (d, J=8.8 Hz, 1H), 7.54 (d, J=8.8 Hz, 1H), 6.94 (s, 1H), 5.06 (s, 2H), 4.10 (s, 2H), 2.76 (d, J=6.0 Hz, 2H), 2.48 (d, J=6.0 Hz, 2H), 2.23 (s, 6H).

ESI$^+$-MS: m/z ESI$^+$-MS: m/z (relative intensity) 313.1 (MH$^+$, 100), 314.1 (18), 315.1 (65), 316.1 (11), 317.1 (11), 318.1 (2). Minor peaks due to fragmentation in the mass spectrometer were detected at m/z 268.0 {M'=[M−(CH$_3$)$_2$N]+, 10}, 224.9 {M"=[M−(CH$_3$)$_2$N—(CH$_2$)$_2$—NH]$^+$, 18}, 190.0 (M"−Cl, 6), 155.0 (M"−2 Cl, 3). Isotopic patterns are consistent. HRMS (ESI$^+$) for C$_{14}$H$_{19}$N$_4$Cl$_2$: Calcd, 313.0987; Found, 313.0990.

Calculated log P=2.42 (ChemDraw Pro, v. 14.0).

Example 4: Synthesis of TDMQ-12

Synthetic route is shown as follows.

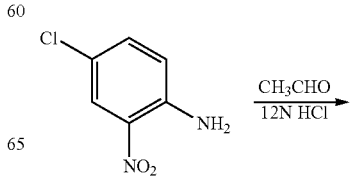

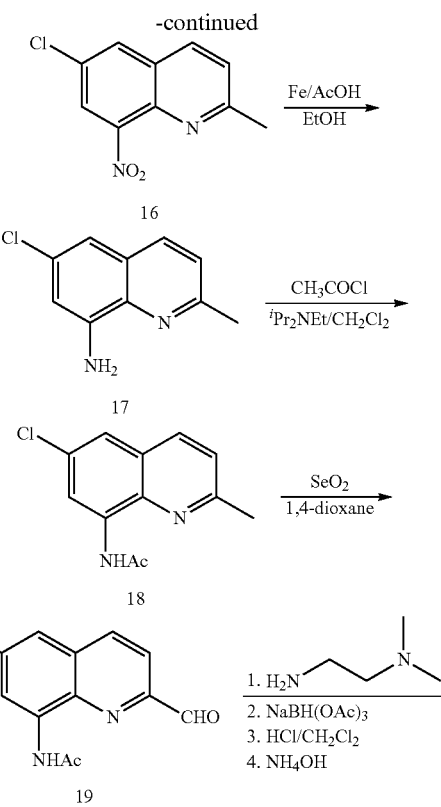

9.79 (s, 1H), 8.75 (s, 1H), 7.94 (d, J=8.0 Hz, 1H), 7.43 (s, 1H), 7.34 (d, J=8.0 Hz, 1H), 2.73 (s, 3H), 2.36 (s, 3H).

N-(6-chloro-2-formylquinolin-8-yl)acetamide (19)

The procedure was similar to that described for the preparation of compound 5. Compound 19 was obtained as a light yellow solid (45%). $^1$H NMR (400 MHz, CDCl$_3$): δ 10.23 (s, 1H), 9.71 (s, 1H), 8.90 (s, 1H), 8.24 (d, J=8.0 Hz, 1H), 8.10 (d, J=8.0 Hz, 1H), 7.57 (s, 1H), 2.42 (s, 3H).

$N^1$-((8-amino-6-chloroquinolin-2-yl)methyl)-$N^2,N^2$-dimethylethane-1,2-diamine (TDMQ-12)

The procedure was similar to that described for the preparation of TDMQ-5. TDMQ-12 was obtained as a light yellow solid (91%). $^1$H NMR (400 MHz, CDCl$_3$) δ 7.89 (d, J=8.4 Hz, 1H), 7.39 (d, J=8.4 Hz, 1H), 7.07 (d, J=2.0 Hz, 1H), 6.83 (d, J=2.0 Hz, 1H), 5.14 (brs, 2H), 4.06 (s, 2H), 2.81 (brs, 1H), 2.77 (t, J=6.0 Hz, 2H), 2.48 (t, J=6.0 Hz, 2H), 2.22 (s, 6H).

Example 5: Synthesis of TDMQ-13

Synthetic route is shown as follows.

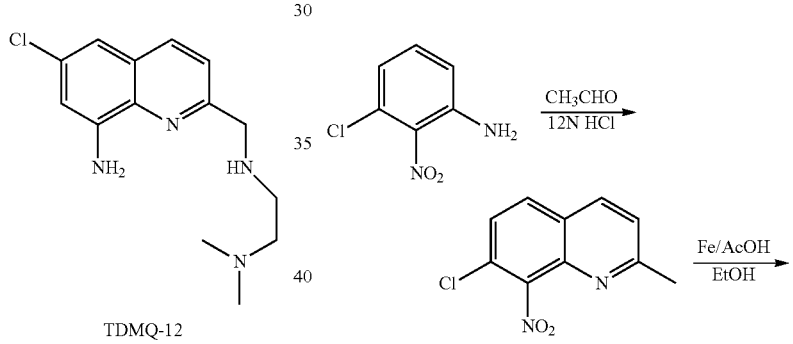

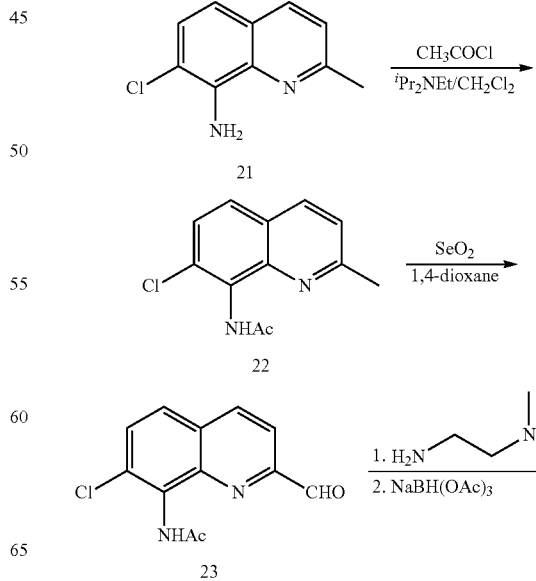

The specific steps are described below.

6-chloro-2-methyl-8-nitroquinoline (16)

The procedure was similar to that described for the preparation of compound 1. Compound 11 was obtained as a light yellow solid (54%). $^1$H NMR (400 MHz, CDCl$_3$): δ 8.04 (d, J=8.4 Hz, 1H), 7.94 (d, J=2.1 Hz, 1H), 7.92 (d, J=2.2 Hz, 1H), 7.44 (d, J=8.4 Hz, 1H), 2.76 (s, 3H).

6-chloro-2-methylquinolin-8-amine (17)

The procedure was similar to that described for the preparation of compound 3. Compound 17 was obtained as a light yellow solid (81%). $^1$H NMR (400 MHz, CDCl$_3$): δ 7.84 (d, J=8.4 Hz, 1H), 7.24 (d, J=8.4 Hz, 1H), 7.06 (d, J=2.0 Hz, 1H), 6.83 (d, J=2.0 Hz, 1H), 5.05 (brs, 2H), 2.68 (s, 3H).

N-(6-chloro-2-formylquinolin-8-yl)acetamide (18)

The procedure was similar to that described for the preparation of compound 8. Compound 11 was obtained as a light yellow solid (81%). $^1$H NMR (400 MHz, CDCl$_3$): δ

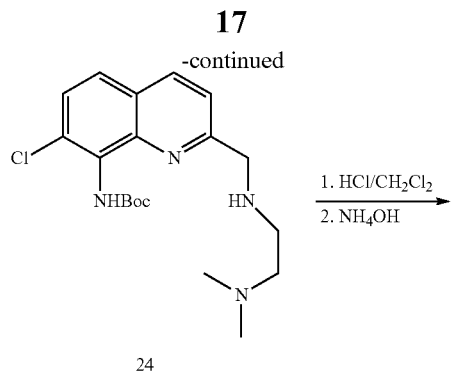

Hz, 1H), 7.43 (d, J=8.4 Hz, 1H), 4.11 (s, 2H), 2.79 (t, J=6.0 Hz, 2H), 2.50 (t, J=6.0 Hz, 2H), 2.239 (s, 6H).

$N^1$-((8-amino-7-chloroquinolin-2-yl)methyl)-$N^2,N^2$-dimethylethane-1,2-dia mine (TDMQ-13)

The procedure was similar to that described for the preparation of TDMQ-5. TDMQ-13 was obtained as a light yellow solid (97%). TDMQ-13: $^1$H NMR (400 MHz, CDCl$_3$) δ 7.99 (d, J=8.4 Hz, 1H), 7.39 (d, J=8.4 Hz, 1H), 7.34 (d, J=8.7 Hz, 1H), 7.05 (d, J=8.7 Hz, 1H), 5.35 (brs, 2H), 4.09 (s, 2H), 2.76 (t, J=6.0 Hz, 2H), 2.48 (t, J=6.0 Hz, 2H), 2.46 (brs, 1H), 2.23 (s, 6H).

Example 6: Synthesis of TDMQ-16

Synthetic route is shown as follows.

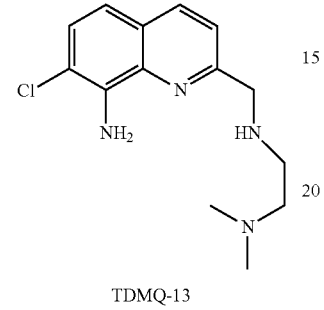

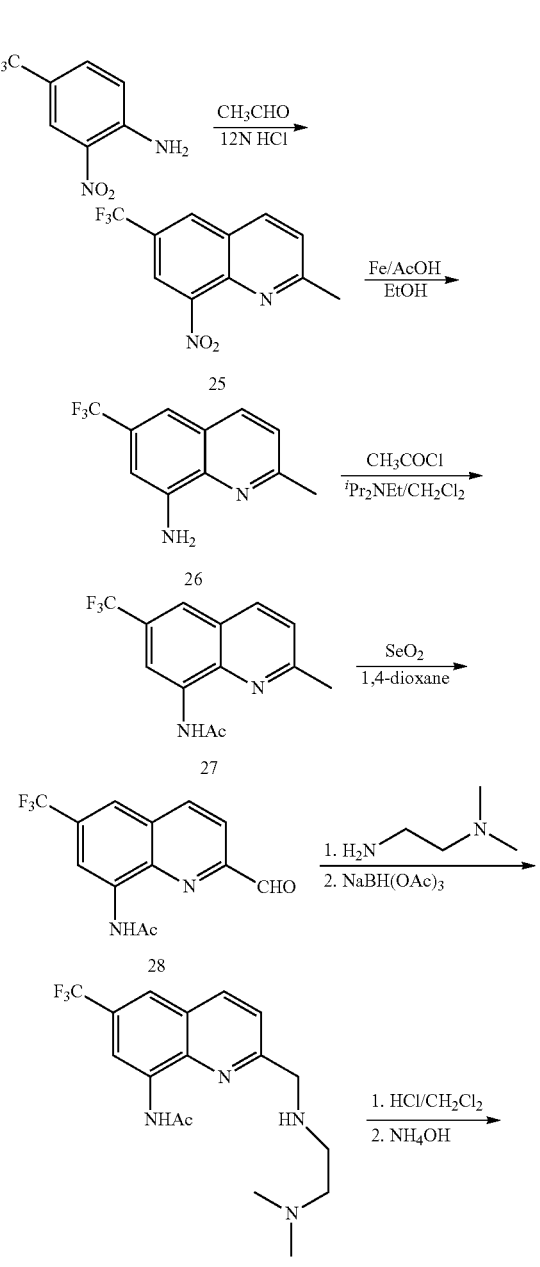

The specific steps are described below.

7-chloro-2-methyl-8-nitroquinoline (20)

The procedure was similar to that described for the preparation of compound 1. Compound 20 was obtained as a light yellow solid (80%). $^1$H NMR (400 MHz, CDCl$_3$) δ 8.08 (d, J=8.5 Hz, 1H), 7.83 (d, J=8.8 Hz, 1H), 7.52 (d J=8.8 Hz, 1H), 7.40 (d, J=8.5 Hz, 1H), 2.74 (s, 3H).

7-chloro-2-methylquinolin-8-amine (21)

The procedure was similar to that described for the preparation of compound 3. Compound 21 was obtained as a light yellow solid (86%). $^1$H NMR (400 MHz, CDCl$_3$): δ 7.84 (d, J=8.0 Hz, 1H), 7.24 (d, J=8.0 Hz, 1H), 7.06 (s, 1H), 6.83 (s, 1H), 5.05 (brs, 2H), 2.68 (s, 3H).

N-(7-chloro-2-methylquinolin-8-yl)acetamide (22)

The procedure was similar to that described for the preparation of compound 8. Compound 22 was obtained as a light yellow solid (42%). $^1$H NMR (400 MHz, CDCl$_3$): δ 8.04 (d, J=8.4 Hz, 1H), 7.79 (d, J=8.8 Hz, 1H), 7.57 (d, J=8.8 Hz, 1H), 7.32 (d, J=8.4 Hz, 1H), 2.688 (s, 3H), 2.298 (s, 6H).

N-(7-chloro-2-formylquinolin-8-yl)acetamide (23)

The procedure was similar to that described for the preparation of compound 5. Compound 23 was obtained as a light yellow solid (64%). $^1$H NMR (400 MHz, CDCl$_3$): δ 10.13 (s, 1H), 8.39 (d, J=8.8 Hz, 1H), 8.10 (d, J=8.8 Hz, 1H), 7.96 (d, J=8.8 Hz, 1H), 7.81 (d, J=8.8 Hz, 1H), 2.330 (s, 6H).

N-(7-chloro-2-(((2-(dimethylamino)ethyl)amino) methyl)quinolin-8-yl)aceta mide (24)

The procedure was similar to that described for the preparation of compound 10. Compound 24 was obtained as a light yellow solid (94%). $^1$H NMR (400 MHz, CDCl$_3$): δ 8.08 (d, J=8.4 Hz, 1H), 7.62 (d, J=8.8 Hz, 1H), 7.54 (d, J=8.8

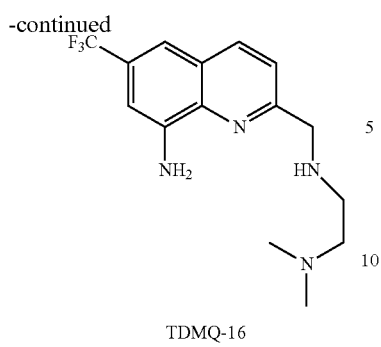

TDMQ-16

The specific steps are described below.

2-methyl-8-nitro-6-(trifluoromethyl)quinoline (25)

The procedure was similar to that described for the preparation of compound 1. Compound 25 was obtained as a light yellow solid (59%). $^1$H NMR (400 MHz, CDCl$_3$) δ 8.28 (s, 1H), 8.22 (d, J=8.4 Hz, 1H), 8.12 (s, 1H), 7.54 (d, J=8.4 Hz, 1H), 2.81 (s, 3H).

2-methyl-6-(trifluoromethyl)quinolin-8-amine (26)

The procedure was similar to that described for the preparation of compound 3. Compound 26 was obtained as a light yellow solid (74%). $^1$H NMR (400 MHz, CDCl$_3$): δ 8.02 (d, J=8.4 Hz, 1H), 7.39 (s, 1H), 7.33 (d, J=8.4 Hz, 1H), 7.01 (s, 1H), 5.15 (brs, 2H), 2.74 (s, 3H).

N-(2-methyl-6-(trifluoromethyl)quinolin-8-yl)acetamide (27)

The procedure was similar to that described for the preparation of compound 8. Compound 27 was obtained as a light yellow solid (78%). $^1$H NMR (400 MHz, CDCl$_3$): δ 9.85 (s, 1H), 8.97 (s, 1H), 8.12 (d, J=8.4 Hz, 1H), 7.76 (s, 1H), 7.42 (d, J=8.4 Hz, 1H), 2.79 (s, 3H), 2.38 (s, 3H).

N-(2-formyl-6-(trifluoromethyl)quinolin-8-yl)acetamide (28)

The procedure was similar to that described for the preparation of compound 5. Compound 28 was obtained as a light yellow solid (50%). $^1$H NMR (400 MHz, CDCl$_3$): δ 10.28 (s, 1H), 9.77 (s, 1H), 9.12 (s, 1H), 8.45 (d, J=8.0 Hz, 1H), 8.18 (d, J=8.0 Hz, 1H), 7.90 (s, 1H), 2.43 (s, 3H).

N-(2-(((2-(dimethylamino)ethyl)amino)methyl)-6-(trifluoromethyl)quinolin-8-yl)acetamide (29)

The procedure was similar to that described for the preparation of compound 10. Compound 29 was obtained as a light yellow solid (96%). $^1$H NMR (400 MHz, CDCl$_3$): δ 9.92 (s, 1H), 9.00 (s, 1H), 8.20 (d, J=8.0 Hz, 1H), 7.79 (s, 1H), 7.61 (d, J=8.0 Hz, 1H), 4.17 (s, 2H), 2.77 (t, J=6.0 Hz, 2H), 2.50 (t, J=6.0 Hz, 2H), 2.36 (s, 3H), 2.24 (s, 6H).

$N^1$-((8-amino-6-(trifluoromethyl)quinolin-2-yl)methyl)-$N^2$,$N^2$-dimehyletha ne-1,2-diamine (TDMQ-16)

The procedure was similar to that described for the preparation of TDMQ-5. TDMQ-16 was obtained as a light yellow solid (99%). TDMQ-16: $^1$H NMR (400 MHz, CDCl$_3$) δ 8.07 (d, J=8.4 Hz, 1H), 7.48 (d, J=8.4 Hz, 1H), 7.39 (s, 1H), 7.01 (s, 1H), 5.23 (brs, 2H), 4.11 (s, 2H), 2.77 (t, J=6.0 Hz, 2H), 2.55 (brs, 1H), 2.48 (t, J=6.0 Hz, 2H), 2.23 (s, 6H).

Example 7: Synthesis of TDMQ-19

Synthetic route is shown as follows.

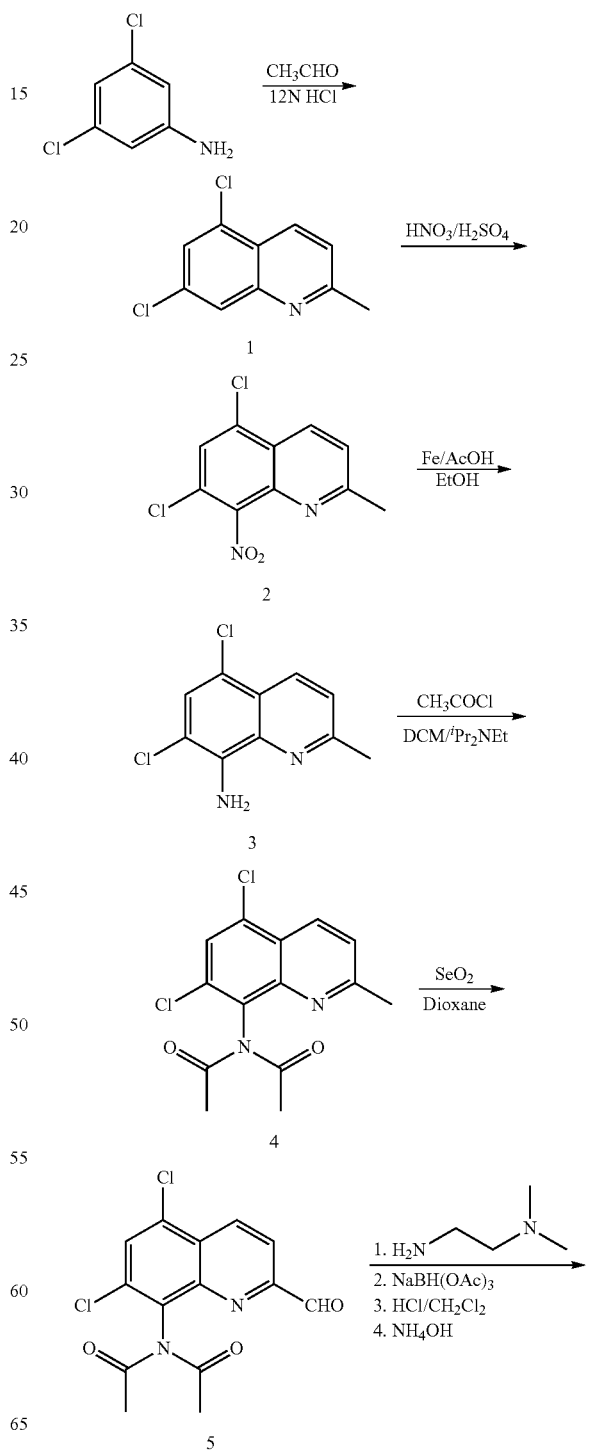

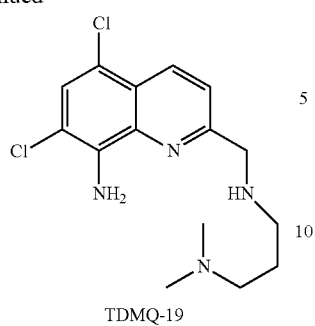

TDMQ-19

The specific steps are described below.

N¹-((8-amino-5,7-dichloroquinolin-2-yl)methyl)-N³, N₃-dimehypropane-1,3-diamine (TDMQ-19)

The procedure was similar to that described for the preparation of TDMQ-5. TDMQ-19 was obtained as a light yellow solid (87%). ¹H NMR (400 MHz, D$_2$O): δ 8.49 (d, J=8.8 Hz, 1H), 7.58 (s, 1H), 7.49 (d, J=8.8 Hz, 1H), 4.58 (s, 2H), 3.25 (t, J=8.0 Hz, 2H), 3.19 (t, J=8.0 Hz, 2H), 2.82 (s, 6H), 2.23-2.15 (m, 2H).

Example 8: Synthesis of TDMQ-20

Synthetic route is shown as follows.

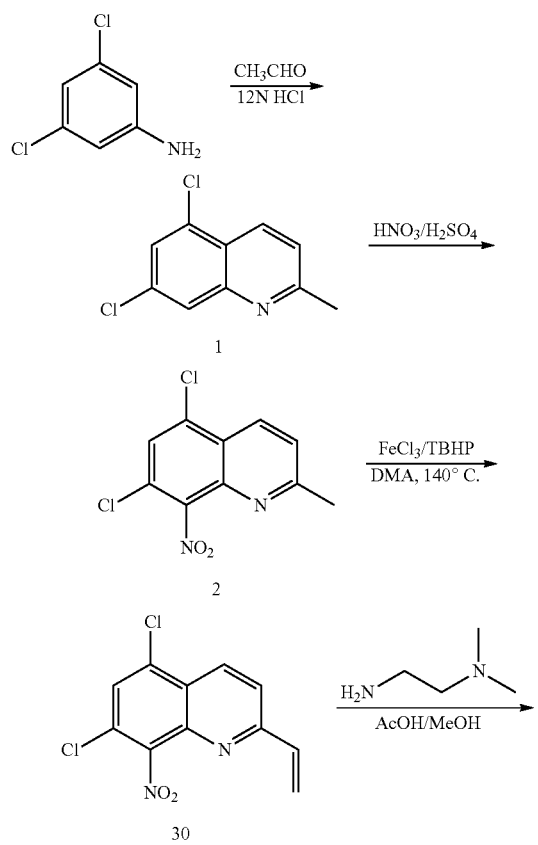

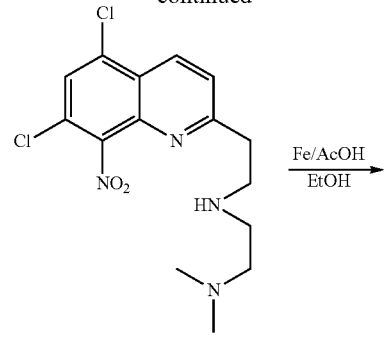

31

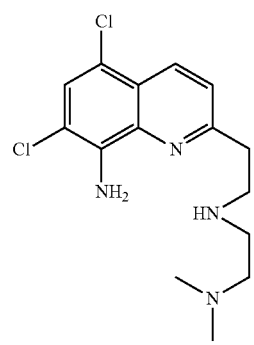

TDMQ-20

The specific steps are described below.

5,7-dichloro-8-nitro-2-vinylquinoline (30)

TBHP (0.6 mmol, 70% aqueous solution) was added to a mixture of FeCl$_3$ (3.2 mg, 0.02 mmol), compound 2 (51.4 mg, 0.2 mmol), and N,N-dimethylacetamide (1 mL). Subsequently, the reaction mixture was heated to 140° C. and stirred at this temperature for 4 h under air. The resulting mixture was then cooled to room temperature, diluted with water, and extracted with dichloromethane. The organic phase was washed with brine and dried over sodium sulfate, and the solvent was evaporated under reduced pressure. The resulting residue was purified by silica gel flash chromatography (EtOAc/petroleum ether, 1:10, v/v) to give compound 30 as a white solid (17.7 mg, 67% based on the conversion of starting material; 51% of the starting material was recovered unchanged). ¹H NMR (400 MHz, CDCl$_3$) δ 8.52 (d, J=8.8 Hz, 1H), 7.73 (d, J=8.8 Hz, 1H), 7.65 (s, 1H), 6.97 (dd, J=17.6, 10.8 Hz, 1H), 6.46 (d, J=17.6 Hz, 1H), 5.79 (d, J=10.8 Hz, 1H).

N¹-(2-(5,7-dichloro-8-nitroquinolin-2-yl)ethyl)-N², N²-dimethylethane-1,2-d iamine (31)

A mixture of compound 30 (1.08 g, 4 mmol), N,N-dimethyl-1,2-ethanediamine (352 mg, 4 mmol), and acetic acid (4 mmol) in methanol (15 mL) was refluxed for 12 h. After removal of the solvent by evaporation, the resulting residue was dissolved in CH$_2$Cl$_2$ (30 mL), and the CH$_2$Cl$_2$ solution was washed with 10% aqueous NaOH three times, and dried over anhydrous K$_2$CO$_3$. After removal of K$_2$CO$_3$ by filtration and evaporation of the organic solvent, compound 31 was isolated by silica gel flash chromatography (ethyl acetate/isopropanol/ammonium hydroxide (25%), 8:2:0.5, v/v/v) as a light yellow solid (75%). ¹H NMR (400

MHz, CDCl$_3$): δ 8.46 (d, J=8.8 Hz, 1H), 7.66 (s, 1H), 7.54 (d, J=8.8 Hz, 1H), 3.22 (t, J=6.0 Hz, 2H), 3.12 (t, J=6.0 Hz, 2H), 2.74 (t, J=6.4 Hz, 2H), 2.43 (t, J=6.4 Hz, 2H), 2.23 (s, 6H).

N$^1$-(2-(8-amino-5,7-dichloroquinolin-2-yl)ethyl)-N$^2$,N$^2$-dimethylethane-1,2-diamine (TDMQ-20)

The procedure was similar to that described for the preparation of compound 3. TDMQ-20 was obtained as a light yellow solid (90%). $^1$H NMR (400 MHz, CDCl$_3$): δ 8.33 (d, J=8.8 Hz, 1H), 7.43 (s, 1H), 7.37 (d, J=8.8 Hz, 1H), 5.40 (brs, 2H), 3.19-3.12 (m, 4H), 2.77 (t, J=6.0 Hz, 2H), 2.44 (t, J=6.0 Hz, 2H), 2.22 (s, 6H).

Example 9: Synthesis of TDMQ-22

Synthetic route is shown as follows.

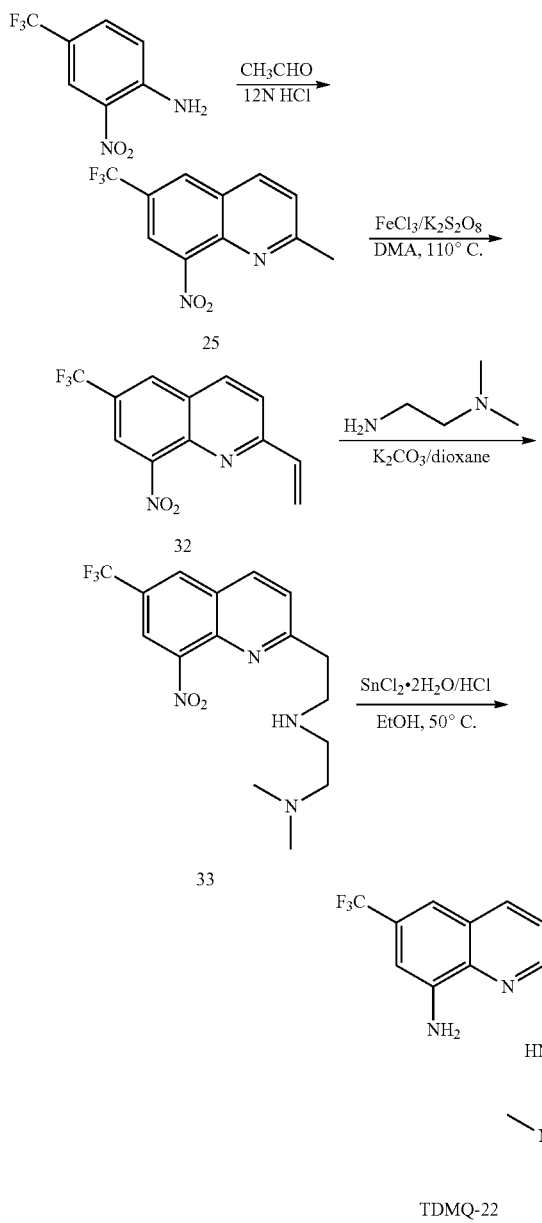

8-nitro-6-(trifluoromethyl)-2-vinylquinoline (32)

To a solution of compound 25 (1.0 g, 3.9 mmol) in DMA (5 mL) was added FeCl$_3$ (19.0 mg, 0.117 mmol) and K$_2$S$_2$O$_8$ (1.05 g, 7.8 mmol). The mixture was stirred at 110° C. for 15 min and quenched with water. After extraction with CH$_2$Cl$_2$, the organic phase was dried over Na$_2$SO$_4$, filtered, and concentrated under reduced pressure. The crude mixture was purified by silica gel flash column chromatography (dichloromethane/hexane, 1:5, v/v). After evaporation of the eluent, compound 32 was obtained as a brown solid (470.7 mg, 45%). $^1$H NMR (400 MHz, CDCl$_3$) δ ppm: 8.30-8.28 (m, 2H), 8.15 (s, 1H), 7.76 (d, J=8.4 Hz, 1H), 7.02 (dd, J=17.6 Hz, 10.8 Hz, 1H), 6.52 (d, J=17.6 Hz, 1H), 5.82 (d, J=10.8 Hz, 1H).

N$^1$,N$^1$-dimethyl-N$^2$-(2-(8-nitro-6-(trifluoromethyl)quinolin-2-yl)ethyl)ethan e-1,2-diamine (33)

To a mixture of compound 32 (388.9 g, 1.45 mmol) and K$_2$CO$_3$ (240.5 g, 1.74 mmol) in 1,4-dioxane (5 mL) was added N,N-dimethyl-1,2-ethanediamine (255.6 mg, 2.9 mmol). The reaction mixture was stirred at room temperature for 1 h, and quenched with water. After extraction with CH$_2$Cl$_2$, the organic phase was dried over Na$_2$SO$_4$, filtered, and concentrated under reduced pressure. The crude mixture was purified by silica gel flash column chromatography (ethyl acetate/isopropanol/ammonium hydroxide (25%), 50:1:1, v/v/v). After evaporation of the eluent, compound 33 was obtained as yellow solid (416 mg, 80%). $^1$H NMR (400 MHz, CDCl$_3$) δ ppm: δ 8.29 (s, 1H), 8.24 (d, J=8.8 Hz, 1H), 8.16 (s, 1H), 7.56 (d, J=8.4 Hz, 1H), 3.26 (t, J=6.4 Hz, 2H), 3.16 (t, J=6.4 Hz, 2H), 2.77 (t, J=6.4 Hz, 2H), 2.44 (t, J=6.4 Hz, 2H), 2.22 (s, 6H).

N$^1$-(2-(8-amino-6-(trifluoromethyl)quinolin-2-yl)ethyl)-N$^2$,N$^2$-dimethyletha ne-1,2-diamine (TDMQ-22)

To a mixture of compound 33 (142.5 mg, 0.4 mmol), SnCl$_2$·2H$_2$O (270.8 mg, 1.2 mmol) in ethanol (5 mL) was added concentrated HCl (1 mL) dropwise at room temperature, and the mixture was stirred at 50° C. for 1 h. Water (50 mL) was added, followed by addition of extra aqueous 25% ammonium hydroxide. The mixture was extracted with CH$_2$Cl$_2$ (3×30 mL). The combined organic layers were dried (Na$_2$SO$_4$), filtered and concentrated under reduced pressure. The crude product was purified by silica gel flash chromatography (ethyl acetate/isopropanol/ammonium hydroxide (25%), 50:1:1, v/v/v). Evaporation of the solvent afforded TDMQ-22 as a light yellow solid (96.6 mg, 74%). $^1$H NMR (400 MHz, CDCl$_3$): δ 8.04 (d, J=8.4 Hz, 1H), 7.38 (s, 1H), 7.35 (d, J=8.4 Hz, 1H), 7.01 (s, 1H), 5.24 (brs, 2H), 3.21-3.11 (m, 4H), 2.78 (t, J=6.0 Hz, 2H), 2.45 (t, J=6.0 Hz, 2H), 2.21 (s, 6H).

Example 10: Experiment of the Derivatives Specifically Chelating Copper Ions Estimation of affinity constants of compounds of general formula (I) with metal ions:
Affinity Constants for $Cu^{2+}$:
The following mother solutions were prepared: (A) ligand L=TDMQ-n, 300 μM in 20 mM Tris.HCl pH 7.4, 150 mM NaCl; (B) Competing ligands (namely NTA, EDTA, EDDA, EGTA, or CDTA), 300 μM in 20 mM Tris.HCl pH 7.4, 150 mM NaCl; (C) CuCl$_2$, 15 mM in H$_2$O. In the UV/Vis cuvette, 100 μL of (A), 100 μL of (B), 1800 μL of 20 mM Tris.HCl pH 7.4, 150 mM NaCl, and 2 μL of (C) were added in that order. The final concentrations of L, Competing ligand (L$_C$), and Cu$^{2+}$ were 15 μM. The spectrum of the mixture was recorded from 250 to 600 nm at room temperature as shown in FIG. 1.

The spectrum of the ligand L (2 μL of H$_2$O instead of 2 μL of (C)) was recorded according to above conditions; and the spectrum of [Cu$^{2+}$-L] (100 μL of 20 mM Tris.HCl pH 7.4, 150 mM NaCl, instead of 100 μL of (B)) was recorded according to above conditions. All ligands and complexes studied followed the Beer-Lambert law in the experimental conditions used.

The equations of complexation are as follows:

$$L + Cu^{2+} \rightleftharpoons Cu-L, \text{ with } K_{app[Cu-L]} = \frac{[Cu-L]}{[Cu][L]}$$

$$L_C + Cu^{2+} \rightleftharpoons Cu-L_C, \text{ with } K_{app[Cu-Lc]} = \frac{[Cu-L_C]}{[Cu][L_C]}$$

It can be deduced that at the equilibrium:

$$K_{app[Cu-L]} = K_{app[Cu-Lc]} \frac{[L_C][Cu-L]}{[L][Cu-L_C]}$$

UV/Vis monitoring at 383 nm allowed to determine the absorbance of the competitive chelation mixture (A$_{mix}$), the absorbance of L in the absence of Cu$^{2+}$ (A$_L$), and the absorbance of CuL in the absence of competing ligand (A$_{Cu-L}$). The proportion of Cu$^{2+}$ chelated by L was calculated as x=(A$_L$-A$_{mix}$)/(A$_L$-A$_{Cu-L}$). Experiments were performed in triplicate.

Affinity Constants for Zn$^{2+}$:

When Ligand-Zn complex (1/1) shows very low affinity, there is equilibrium in the solution under the same reaction condition:

$$L + Zn^{2+} \rightleftharpoons Zn-L, \text{ with } K_{app[Zn-L]} = \frac{[Zn-L]}{[Zn][L]}$$

As TDMQs ligands exhibit a much lower affinity for Zn$^{2+}$ compared to Cu$^{2+}$, at 10-20 mM, there is equilibrium in the solution between the free ligand L and the Zn-L complex (stoichiometry L/Zn=1/1). So, K$_{app}$[Zn-L] can be calculated by titration of L with sequential additions of a Zn$^{2+}$ salt, without using of a competing ligand:

$$L + Zn^{2+} \rightleftharpoons Zn-L, \text{ with } K_{app[Zn-L]} = \frac{[Zn-L]}{[Zn][L]}$$

TABLE 1

Affinity constants of the different ligands for Cu$^{2+}$ or Zn$^{2+}$ ions at pH = 7.4

| Ligand | Log KCu$^{2+}$ | Log KZn$^{2+}$ |
|---|---|---|
| TDMQ-5 | 9.8 | 4.2 |
| TDMQ-9 | 10.2 | 4.7 |
| TDMQ-10 | 9.7 | 4.5 |

TABLE 1-continued

Affinity constants of the different ligands for Cu$^{2+}$ or Zn$^{2+}$ ions at pH = 7.4

| Ligand | Log KCu$^{2+}$ | Log KZn$^{2+}$ |
|---|---|---|
| TDMQ-12 | 10.2 | 4.7 |
| TDMQ-13 | 10.4 | 4.6 |
| TDMQ-16 | 10.0 | 4.5 |
| TDMQ-19 | 10.2 | negligible (~0) |
| TDMQ-20 | 16.5 | 4.2 |
| TDMQ-22 | 15.1 | 4.1 |

The results of Table 1 show that the binding constant of the derivatives in the present disclosure for copper log K$_{cu}^{2+}$ is higher than 9.7, and up to 16.5, while the binding constant for zinc log K$_{zn}^{2+}$ is below 4.7 according to the calculation to the binding constants of copper(II) and zinc(II) for a series of TDMQ chelators. For example, the binding constant of TDMQ-19 for zinc is negligible, namely the TDMQ-19 cannot significantly chelate zinc ions. The binding constant of TDMQ-19 for copper is 10.2. The difference between the two binding constant is 10 orders of magnitude. The affinity constants of TDMQ-20 for copper and zinc are 16.5 and 4.2, respectively, and the difference between them is 12 orders of magnitude. It shows that the derivatives in the present disclosure are able to selectively chelate copper ions with respect to zinc, and can be used for manufacturing drugs for neurodegenerative diseases and diseases related to disorder of copper metabolism.

Example 11: Quantitative Analysis of the Hydrogen Peroxide Produced by Aβ in the Presence of Cu$^{2+}$, Reducing Agent with or without TDMQ Ligand The production of H$_2$O$_2$ was quantified by fluorescence, using the Red Hydrogen Peroxide Assay kit from Enzo Life Sciences (Cat.=ENZ-51004 Lot No. 10231415). Fluorescence spectra were recorded on a FLSP920 spectrometer (Edinburgh Instruments), with bandwidth for excitation and emission=2 nm, λ$_{ex}$=540 nm, λ$_{em}$=584 nm, acquisition range=550-700 nm), repeats: 3 scans for each acquisition.

Stock solutions were: CuCl$_2$ (10 μM in water), Aβ$_{1-16}$ (10 μM in water), TDMQ-5.HCl (10 μM in water), TDMQ-10.HCl (10 μM or 20 μM in water), sodium ascorbate (100 μM in water), Hepes buffer 0.1 M pH 7.4.

In a typical reaction, operations were introduced in the following order: Hepes buffer (50 μL), CuCl$_2$ (10 μL), Aβ$_{1-16}$ (10 μL), 30 min of incubation to form the Cu$^{2+}$-Aβ$_{1-16}$ complex. The solution of TDMQ was then added (10 μL or 20 μL for 1 or 2 mol equiv with respect to Cu$^{2+}$, respectively), incubation for 30 min; ascorbate (10 μL); H$_2$O (sufficient volume to adjust final volume to 100 μL), then incubation for 30 min. Final concentrations were Cu$^{2+}$/Aβ$_{1-16}$/TDMQ/ascorbate/Hepes buffer=1 μM/1 μM/1 μM or 2 μM/10 μM/50 mM. The production of H$_2$O$_2$ was then quantified by fluorescence using the Red Hydrogen Peroxide Assay kit according to the protocol of the supplier (λ$_{ex}$=540 nm, λ$_{em}$=550-700 nm). Reaction mixtures were incubated for 30 min, protected from light before measure.

Figure 2:
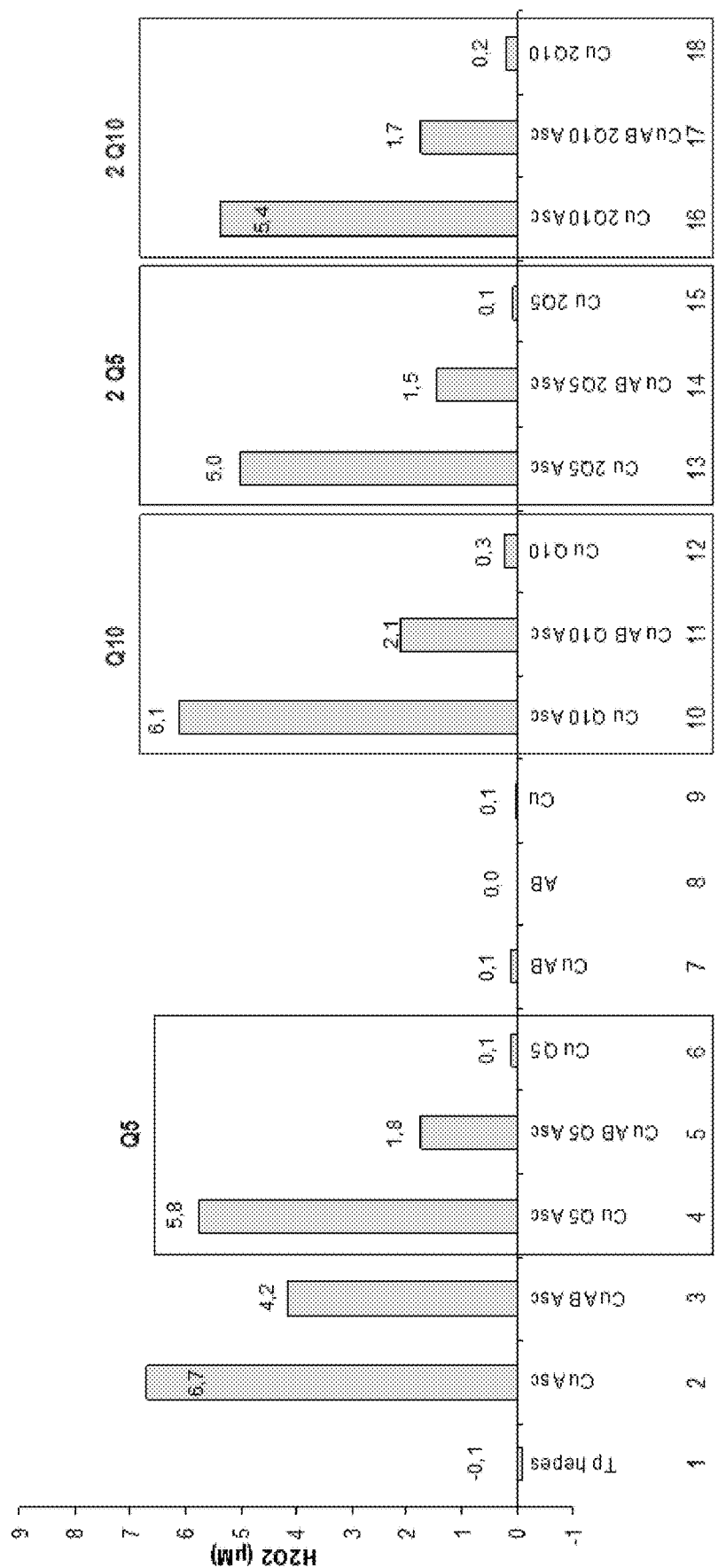
FIG. 2 is the inhibition of production of $H_2O_2$ induced by the copper complexes of amyloid-β associated to ascorbate, in the presence of TDMQ-5 (indicated as Q5) or TDMQ-10 (indicated as Q10).

Control experiments were: Cu-Aβ$_{1-16}$±ascorbate, CuCl$_2$±ascorbate, Aβ$_{1-16}$ or C$^{2+}$ alone, performed in the same conditions. Results are shown in FIG. 2.

Through the experiments on production of hydrogen peroxide by amyloid-β in the presence of copper ions and a reducing agent, it finds that the derivatives in the present invention are able to extract copper from copper-amyloid protein and exhibit a strong capability of reducing an oxidative stress.

We claim:

1. A tetradentate chelating monoquinoline derivative, wherein a structure of the derivative is as shown in formula (I):

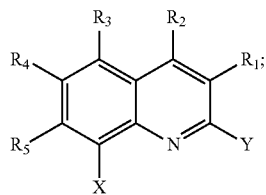

formula (I)

X represents a NRR' group;

Y represents a group with the following formula: —$(CH_2)_n$—$NR_6$—$(CH_2)_m$—$NR_7R_8$; n represents 1 or 2 or 3 or 4 or 5, m represents 1 or 2 or 3 or 4 or 5;

R and R' are the same or different and independently represent a hydrogen atom, or $C_{1-6}$ alkyl, or $C_{3-6}$ cycloalkyl or —$CF_3$, or a halogen atom, or —CN, or —OH;

$R_6$ represents hydrogen atom, or $C_{1-6}$ alkyl, or $C_{3-6}$ cycloalkyl, or $CF_3$ or an halogen atom;

the definition of $R_7$ or $R_8$ is the sane as that of $R_6$;

$R_1$, $R_2$, $R_3$, $R_4$ and $R_5$ are the same or different and independently represent a group or an atom selected from H or a halogen atom, or —CN, or —$CF_3$, or —OH, or $C_{1-6}$ alkyl, or $C_{3-6}$ cycloalkyl.

2. The tetradentate chelating monoquinoline derivative of claim 1, wherein X represents an —$NH_2$.

3. A pharmaceutical composition of a compound or a pharmaceutically acceptable salt thereof of formula (I) as claimed in claim 1 and a pharmaceutically acceptable diluent.

* * * * *